United States Patent [19]
Myers et al.

[11] Patent Number: 5,716,395
[45] Date of Patent: Feb. 10, 1998

[54] PROSTHETIC VASCULAR GRAFT

[75] Inventors: David J. Myers, Camp Verde; James D. Lewis, Flagstaff, both of Ariz.

[73] Assignee: W.L. Gore & Associates, Inc., Newark, Del.

[21] Appl. No.: 705,912

[22] Filed: Aug. 27, 1996

Related U.S. Application Data

[63] Continuation of Ser. No. 394,057, Feb. 24, 1995, abandoned, which is a continuation of Ser. No. 989,442, Dec. 11, 1992, abandoned.

[51] Int. Cl.⁶ .................................................. A61F 2/06
[52] U.S. Cl. ........................................................ 623/1
[58] Field of Search ................................ 623/1, 11, 12; 600/36; 606/191–200

[56] References Cited

U.S. PATENT DOCUMENTS

| | | |
|---|---|---|
| 3,953,566 | 4/1976 | Gore. |
| 4,084,266 | 4/1978 | Poirier et al.. |
| 4,130,904 | 12/1978 | Whalen. |
| 4,187,390 | 2/1980 | Gore. |
| 4,323,525 | 4/1982 | Bornat. |
| 4,416,028 | 11/1983 | Eriksson et al.. |
| 4,475,972 | 10/1984 | Wong. |
| 4,619,641 | 10/1986 | Schanzer ............................. 604/8 |
| 4,632,842 | 12/1986 | Karwoski et al.. |
| 4,652,263 | 3/1987 | Herweck. |
| 4,718,907 | 1/1988 | Karwoski et al.. |
| 4,738,740 | 4/1988 | Pinchuk. |
| 4,743,250 | 5/1988 | Kitagawa. |
| 4,850,999 | 7/1989 | Planck. |
| 4,877,661 | 10/1989 | House et al.. |
| 4,878,908 | 11/1989 | Martin et al.. |
| 4,969,896 | 11/1990 | Shors. |
| 5,024,671 | 6/1991 | Tu et al.. |
| 5,026,513 | 6/1991 | House et al.. |
| 5,061,276 | 10/1991 | Tu et al.. |
| 5,100,422 | 3/1992 | Berguer et al.. |
| 5,116,360 | 5/1992 | Pinchuk et al.. |
| 5,192,310 | 3/1993 | Herweck et al.. |
| 5,246,452 | 9/1993 | Sinnott. |
| 5,269,810 | 12/1993 | Hull et al. .............................. 128/639 |

FOREIGN PATENT DOCUMENTS

| | | |
|---|---|---|
| 047231 | 3/1982 | European Pat. Off.. |
| 0117072 | 1/1984 | European Pat. Off.. |
| 0160483 | 4/1985 | European Pat. Off.. |
| 0407692 | 7/1989 | European Pat. Off.. |
| 2015118 | 9/1979 | United Kingdom. |
| 2092894 | 8/1982 | United Kingdom. |
| 8201647 | 5/1982 | WIPO. |

*Primary Examiner*—Debra S. Brittingham
*Attorney, Agent, or Firm*—Wayne D. House

[57] ABSTRACT

A vascular graft in the form of a tube or flat sheet of biocompatible material having an outer covering of deflectably secured material such as porous film, fibers, discrete pieces of material, or combinations thereof. The vascular graft may be of tubular form for replacing or bypassing entire segments of veins or arteries or alternatively may be in the form of a flat sheet useful for repairing portions of the circumference of veins or arteries. The tube or flat sheet of biocompatible material and the outer covering of deflectably secured material are preferably of porous polytetrafluoroethylene. The inventive vascular graft is useful for dialysis access in that it offers a reduction in blood leakage when the vascular graft is punctured by a dialysis needle and the needle is subsequently removed. It is also useful for reducing suture hole bleeding resulting from holes created through the graft by penetration of the graft with a suture needle.

26 Claims, 7 Drawing Sheets

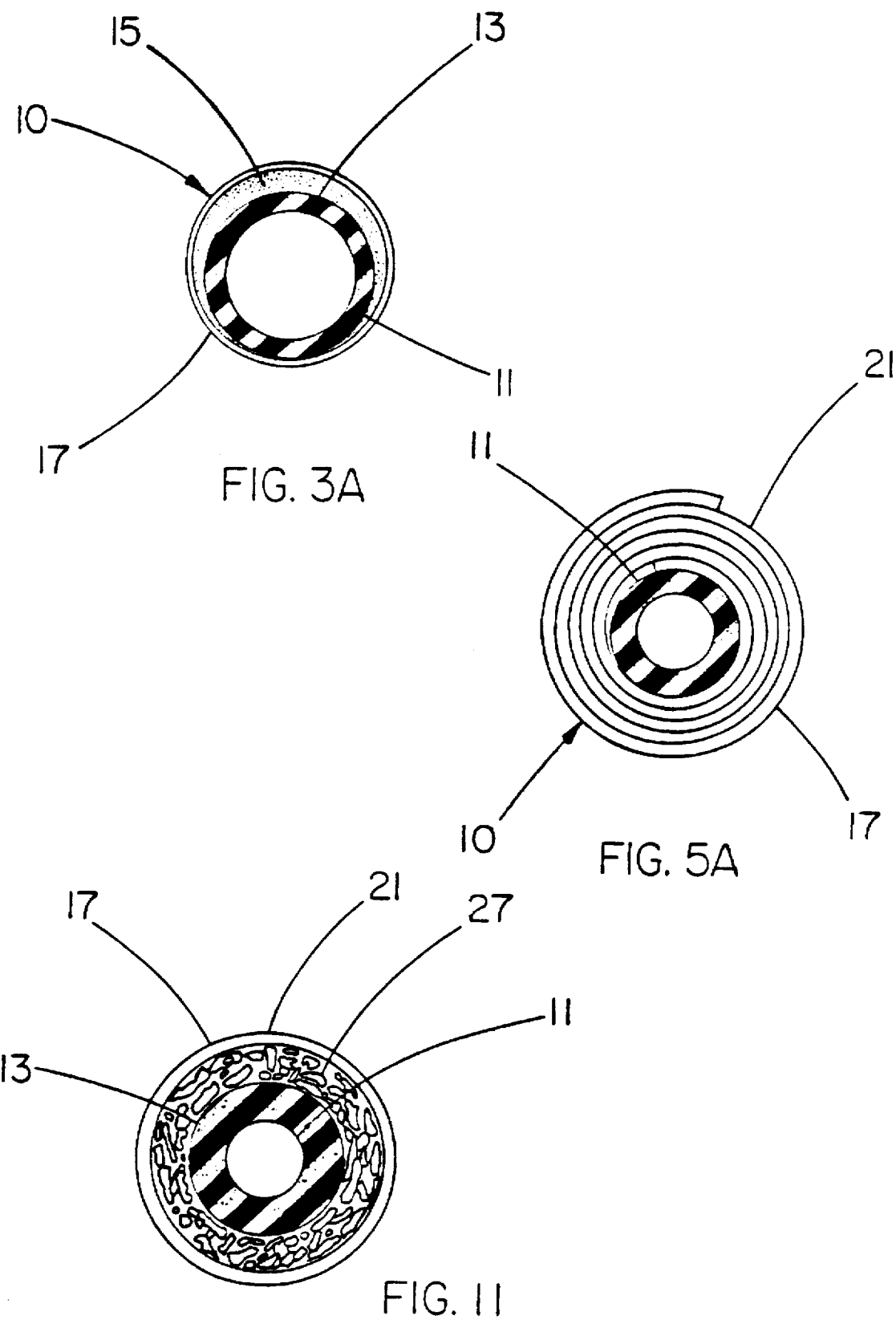

PROSTHETIC VASCULAR GRAFT

This application is a continuation of application Ser. No. 08/394,057 filed Feb. 24, 1995, now abandoned, which is a continuation of Ser. No. 07/989,442 filed Dec. 11, 1992, now abandoned.

FIELD OF THE INVENTION

The present invention relates to the field of prosthetic vascular grafts.

BACKGROUND OF THE INVENTION

A common problem with vascular grafts is bleeding through holes punctured through the wall of a graft by suture needles or dialysis needles. These vascular grafts are most conventionally made of polyethylene terephthalate fabric or porous polytetrafluoroethylene tubing but materials of biologic origin such as human or bovine arteries or veins are also used. Suture needles used to create an anastomosis with these vascular grafts inevitably result in significant bleeding through the resulting holes that must be stopped prior to closure of the operative incision. Dialysis treatment of individuals suffering from renal failure requires that the blood of the individual be withdrawn, cycled through a dialysis machine and returned to the individual. A common approach to providing the necessary hemodialysis access is the use of an implanted arteriovenous vascular graft which may be subcutaneously pierced by a dialysis needle connected to the dialysis machine via a length of tubing.

Vascular grafts presently used for hemodialysis access can be improved in two regards. First, they typically must be implanted for about 14 days prior to puncture with a dialysis needle so that the graft has had time to become surrounded by fibrotic tissue and thereby reduce the risk of hemorrhage about the outer surface of the graft following removal of the dialysis needle. Second, these conventional grafts typically require the use of direct pressure to the puncture site for times in excess of three minutes in order to stop bleeding following removal of the needle. An arteriovenous graft that offered an improvement of either of these regards without compromising other positive characteristics would be a significant step forward in the field of hemodialysis access.

A proposed improvement in the field of arteriovenous access vascular grafts is described by U.S. Pat. No. 4,619,641 which teaches the construction of an access graft comprising two expanded polytetrafluoroethylene grafts in coaxial relationship with a space of about 1 mm disposed between the inner and outer grafts. The space is filled with a self-sealing elastomer such as silicone. While this construction does offer reduced bleeding after withdrawal of a dialysis needle, it is stiff and consequently difficult to work with during implantation.

Suture line bleeding resulting from graft penetration by a suture needle is frequently aggravated by tension applied to the sutures during construction of the anastomosis, the tension generally resulting in elongation and enlargement of the hole created by the penetration of the suture needle. Bleeding through suture holes must be stemmed before the access incision can be closed. Suture hole bleeding is thus responsible for both increased blood loss and increased time of operation. A vascular graft offering reduced suture bleeding would be of value in both regards.

U.S. Pat. No. 5,100,422 describes a blood vessel patch in the form of a sheet of porous polytetrafluoroethylene having an adhered exterior surface coating of an elastomer such as silicone or polyurethane wherein the coating is intended to reduce suture hole bleeding. The use of such coatings adversely affects the porosity of the patch material.

One embodiment of the present invention incorporates the use of fibers with conventional vascular graft constructions. Fibers have a long history of use in the construction of artificial vascular grafts. These devices were originally manufactured from polyethylene terephthalate (hereinafter PET) fibers woven or knitted into tubular forms. PET vascular grafts are rarely used for dialysis access. Further, PET grafts require pre-clotting with the patient's blood prior to implantation in order to avoid bleeding through the spaces between adjacent fibers.

U.S. Pat. No. 4,130,904 describes a double-walled vascular graft comprising two concentrically associated PET fabric tubes with a helical metal spring disposed between the inner and outer tubes. The intended purpose was to produce a crush resistant vascular graft without an exposed, external stiffening component. Various patents have taught the use of electrostatic spinning techniques to manufacture vascular grafts from fibers. U.S. Pat. No. 4,323,525 teaches this technique as a method of forming a graft around a spinning mandrel or form that is removed after the tubular graft is formed. The fibers are formed from a solution or dispersion of a polymer that hardens and adheres to adjacent fibers after the forming of the graft, thereby creating a coherent tube.

U.S. Pat. No. 4,475,972 describes a vascular graft made by helically wrapping thermoplastic fibers in alternating directions about a mandrel and solvent bonding the contact points of overlying fibers. EP 0,407,692 describes a vascular graft comprising at least one tubular sleeve made according to U.S. Pat. No. 4,475,972 fitted coaxially over an inner vascular graft of biologic or synthetic material.

U.S. Pat. Nos. 4,632,842; 4,652,263; and 4,718,907 describe a method of providing longitudinal extensibility to otherwise substantially inextensible vascular graft tubes of woven PET fibers. The method comprises placing such a substantially inextensible tube of woven PET onto a close-fitting mandrel and compressing the tube longitudinally, thereby causing the longitudinally oriented warp fibers to be formed into loops that extend outwardly away from the surface of the mandrel. The compressed tube is then heat-set while still on the mandrel to provide a memory to the formed loops. After cooling and subsequent removal from the mandrel, the woven tube has a degree of longitudinal extensibility because the formed loops are extensible. This product is commercially available in the form of a tube woven from PET thread and provided with a lumenal coating of a fluorine-containing polymer applied by plasma polymerization techniques. Advertising literature for this product states that the fibers from which the tube is woven are punctured during cannulation and subsequently stretch back into place, apparently due to the loops formed into the warp threads.

U.S. Pat. No. 4,878,908 describes a vascular graft made from electrostatically spun fibers and having an inner blood contacting surface comprising fibers. The spun fiber tubular device may be either a self-supporting tube or may be a tubular liner for the interior of a second tubular structure. The fibers are of an organic material and are preferably synthetic materials such as PET, polytetrafluoroethylene (hereinafter PTFE) and silicone.

U.S. Pat. No. 5,061,276 describes a vascular graft comprising a composite tube of expanded PTFE and an elastomer, having an outer layer of elastomeric polymer fibers wound under tension about the circumference of the graft to cause retraction of the tubing from its original size.

The wrapping of elastomeric fibers is provided with the intention of making the graft more compliant.

U.S. Pat. No. 5,116,360 teaches the construction of a composite vascular graft having an inner layer made of wound criss-crossing layers of fibers, an intermediate bonding layer of criss-crossing thermoplastic fibers of lower melt-point than the other construction materials, and an outer layer of porous mesh.

SUMMARY OF THE INVENTION

The present invention relates to a prosthetic vascular graft that offers a reduction in blood loss when the graft is punctured by a dialysis needle or suture needle and the needle is subsequently removed. The graft comprises a tube or flat sheet of biocompatible material (hereinafter referred to as a base substrate regardless of whether the form is that of a tube or flat sheet) wherein a substantial portion of the outer surface of the base substrate is provided with an outer covering of deflectably secured material that is substantially non-adhered or otherwise not directly secured to the outer surface of the base substrate. This substantial portion is deflectable with respect to the outer surface of the substrate, meaning that this substantial portion is movable with respect to the outer surface of the base substrate and moves with respect to the base substrate when both the substantial portion of deflectably secured material and the base substrate are pierced by a needle. This capacity for relative movement allows the deflectably secured material to provide a baffling effect against blood leakage when the needle is removed.

The outer surface of the base substrate is herein defined as the ablumenal side of the base substrate, that is, the side opposite the lumenal, blood contacting side of the base substrate. The inner surface of the deflectably secured material is substantially in direct contact with the ablumenal surface of the base substrate. The deflectably secured material is preferably in the form of a deflectably secured outer covering of porous film, fibers, discrete pieces of material or combinations thereof. These various forms of deflectably secured materials may be present in multiple layers such as, for example, multiple layers of porous film. The various forms may also be applied in side-by-side arrangements such as, for example, fibers adjacent to and either in contact with or in close proximity to each other. Thus these various forms of deflectably secured materials have adjacent surfaces that are either in contact with or in close proximity to each other. A substantial portion of the adjacent surfaces of adjacent layers of film, adjacent fibers and adjacent discrete pieces of material are non-adhered or otherwise not directly secured in order that these adjacent surfaces are capable of relative motion caused by a penetrating needle. For example, if most of the contact points of adjacent fibers of a covering are adhered to each other by an adhesive or by solvent welding, such fibers do not meet the present definition of deflectably secured materials.

The base substrate of biocompatible material is preferably of a polymeric material such as PET fabric or porous PTFE but alternatively may also be a material of biological origin such as harvested bovine or human blood vessels. The base substrate is most preferably a porous, non-fabric substrate such as porous expanded PTFE made as taught by U.S. Pat. No. 4,187,390.

Vascular grafts of the present invention can be of either tubular or flat sheet forms. Tubular vascular graft repair materials are used to replace or bypass entire lengths of tubular veins or arteries while the flat sheet materials, conventionally called vascular patches or cardiovascular patches, are used to replace only a portion of the circumference of a vein or artery. The scope of the present invention includes both tubular vascular grafts and flat sheet vascular patches having an outer covering of deflectably secured material. The use of the term vascular grafts herein includes both tubular and flat sheet forms.

The deflectably secured material is required to be relatively flexible. For example, non-porous, relatively rigid polymeric material adhered to the ablumenal surface of a base tube such as plastic reinforcing rings or spirals, or relatively stiff wires such as the helical spring described by U.S. Pat. No. 4,130,904, intended to provide the base tube with increased rigidity and crush-resistance, are not within the scope of the deflectably secured materials for use with the present invention.

By deflectably secured is meant that the deflectably secured material is secured to the ablumenal surface of the base substrate in a manner that allows a substantial portion of the deflectably secured material to move with respect to the ablumenal surface of the base substrate when the base substrate is pierced with a needle. The deflectably secured material is preferably secured to the base substrate only enough that it be minimally retained to the surface of the base substrate in order to prevent the deflectably secured outer covering from becoming entirely removed from the base substrate. The deflectably secured material is therefore non-adhered or otherwise not directly secured to the ablumenal surface of the base substrate in any manner that precludes relative movement between the base substrate ablumenal surface and the deflectably secured covering for most of the length of the covering material. It is believed that deflectably securing the fibers, film, discrete pieces or combinations thereof, for example by attaching fibers to the ablumenal surface of the base substrate only at the fiber ends, allows the deflectably secured material to deflect aside and away from the surfaces of a needle that is used to penetrate the base substrate. It is also believed that the deflectably secured material in the vicinity of a dialysis needle or suture needle hole through the base substrate serves as a baffle to blood attempting to escape through the needle hole.

An alternative means for deflectably securing the outer covering of fibers, film, discrete pieces, or combinations thereof, is a thin exterior wrapping of porous film applied around the ablumenal surface of the outer covering and which retains the outer covering to the ablumenal surface of the base substrate with only a limited amount of restraint thereby allowing the outer covering to function in a deflectable manner. Suitable films include films of porous expanded PTFE having a microstructure of nodes interconnected by fibrils, made as taught by U.S. Pat. No. 4,187,390. Films of this type may be cut into long, narrow lengths of tape for convenient application by helically wrapping the tape about the outer surface of the fibers with the ends of the tape secured by various methods. An exterior wrapping of such a film is considered to be a part of the outer covering of deflectably secured material in that the exterior wrapping of film is non-adhered or otherwise not directly secured to the ablumenal surface of the base substrate for a substantial portion of the length of the film.

Alternatively, the covering of deflectably secured material applied about the ablumenal surface of the base substrate may be in the form of a film only, wherein the film is preferably applied in the form of a helically wrapped tape. The film or tape is deflectably secured meaning that a substantial portion of the film or tape is non-adhered or otherwise not directly secured to the ablumenal surface of the base substrate. Such a film covering has a loose feel as opposed to a film covering that is substantially adhered to the base substrate. It is preferred that multiple layers of deflectably secured film or tape, for example, five or more layers as counted through any cross section, are applied about the ablumenal surface of the base substrate. It is believed that the presence of the deflectably secured film or tape provides a baffling effect to blood attempting to escape from the hole created in the surface of the base substrate by penetration and removal of a needle. The deflectably secured film or tape is preferably porous expanded PTFE made as taught by U.S. Pat. No. 4,187,390. Alternatively, the film or tape may be of other porous biocompatible material such as a tape of PET fabric. Films and tapes will hereinafter be described only as films.

A preferred film is the porous expanded PTFE film described previously with the addition of a discontinuous thermoplastic adhesive which is preferably a thermoplastic fluoropolymer and most preferably fluorinated ethylene propylene (hereinafter FEP). The thermoplastic adhesive deflectably secures the film to the base substrate by heating the film to a temperature greater than the melting point of the thermoplastic but less than the crystalline melt temperature of the porous PTFE. Processing below this temperature minimizes shrinkage of the porous PTFE portion of the film and, in conjunction with the discontinuous nature of the thermoplastic, allows the film to remain in a loose and deflectably secured condition if the film was applied with little tension about the ablumenal surface of the base substrate. The adhesive-coated film substantially retains the porosity of the porous PTFE precursor film because of the discontinuous nature of the thermoplastic adhesive.

In still another alternative embodiment, the outer covering of deflectably secured material may be in the form of discrete pieces such as pieces of shredded porous PTFE tubing or sheet material deflectably secured to the ablumenal surface of the base substrate by an exterior wrapping of a porous film.

The highly porous nature of the preferred materials used for the outer covering of the base substrate is expected to allow for tissue ingrowth into the ablumenal surface of the inventive graft.

It is anticipated that the vascular graft of the present invention may be provided with rapid recovery characteristics as taught by U.S. Pat. Nos. 4,877,661 and 5,026,513, herein incorporated by reference. These patents describe a process of providing porous PTFE base substrates of either tubular or flat form with rapid recovery characteristics wherein the resulting base substrates at ambient temperature are capable of being stretched and then rapidly recovering more than about 6% and preferably more than about 10% of their stretched length.

The vascular graft of the present invention may optionally be impregnated with various chemical agents such as antimicrobials or antibiotics.

BRIEF DESCRIPTION OF THE DRAWINGS

FIG. 3A describes a cross sectional view of an alternative to the embodiment described by FIG. 3 wherein only the surface of the base tube closest to the skin of the patient has an outer fiber covering.

FIG. 5A shows a cross section of the embodiment wherein the deflectably secured material used as the outer covering of the base tube is in the form of multiple layers of deflectably secured porous film.

FIG. 11 shows a cross sectional view of one embodiment of the present invention having a substantial portion of its length provided with an outer covering of discrete pieces of material deflectably secured by an exterior wrapping of porous film.

DETAILED DESCRIPTION OF THE INVENTION

Figure 1:
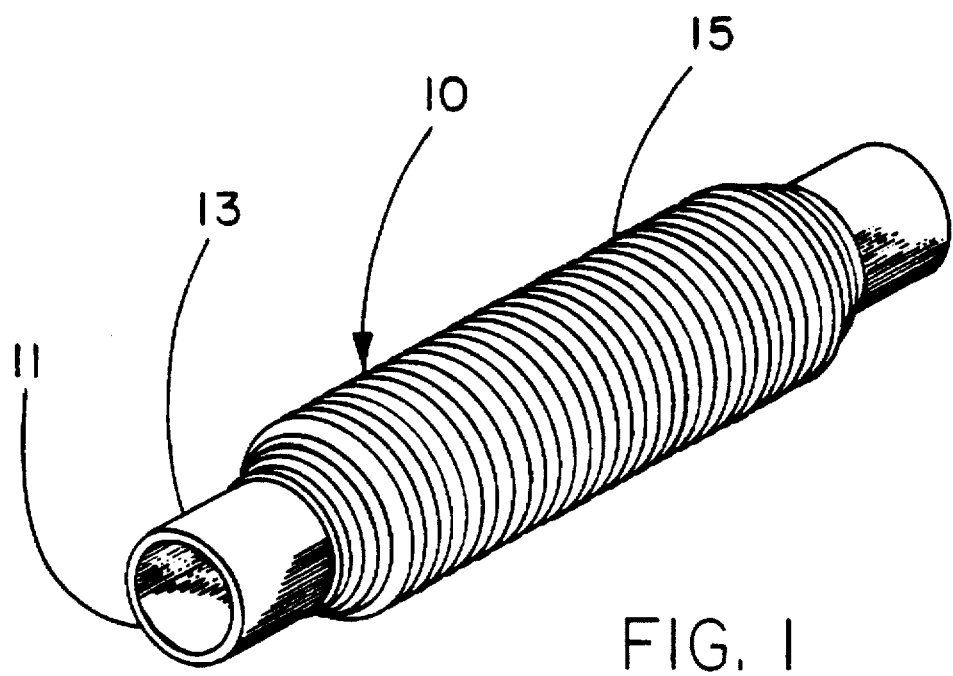
FIG. 1 describes a perspective view of one embodiment of the present invention in the form of a base tube having a substantial portion of its length provided with an outer covering of circumferentially oriented and deflectably secured fiber or fibers.

The base substrate for the subsequently applied outer covering of fibers, film, discrete pieces, or combinations thereof, and which comprises the blood contacting surface of the inventive vascular graft, is preferably porous PTFE. Base substrates of this type are commercially available from W. L. Gore & Associates, Inc. (Flagstaff, Ariz.) and sold under the trade names GORE-TEX® Vascular Graft and GORE-TEX® Cardiovascular Patch. Alternatively the base substrate may be a tube or sheet of woven or knitted fibers of PET, which should preferably be provided with a biocompatible coating such as collagen or gelatin to reduce or eliminate the need for pre-clotting with the patient's blood. In still another alternative, the base substrate may be a material of biologic origin such as harvested bovine or human blood vessels.

The fibers for use as the covering material may be of any suitable biocompatible material. They may consist of single strands or alternatively may be of multiple strands such as small strings or yarns. The fibers themselves may be porous or non-porous. Preferred materials include fibers of PET and PTFE.

The fibers are preferably of non-elastomeric materials. Elastomeric materials are herein defined as polymeric materials which at room temperature can be stretched under low stress to at least twice their original length and, immediately upon release of the stress, will recover with force to their approximate original length. If it is desired to use elastomeric fibers to construct the vascular graft of the present invention, the fibers must be applied to the base substrate with little or no tension in order to be deflectably secured and a substantial portion of the length of the fibers must not be adhered to the ablumenal surface of the base substrate.

The fibers covering the base substrate are preferably substantially parallel to each other, which means that they may be applied to the ablumenal surface of the base substrate either individually or in groups or bundles of fibers that are substantially but not necessarily precisely parallel to each other. The fibers are also applied to the ablumenal surface of the base substrate so that they are substantially parallel to the surface, that is, substantially in contact with or parallel to the curved ablumenal surface, as well as substantially parallel to each other. The fibers may thus be wound about the ablumenal surface of the base substrate with an only slight helical orientation, or may be wound about the ablumenal surface of the base substrate with a substantial helical orientation, or may be applied to the ablumenal surface of the base substrate so that they are oriented substantially parallel to the longitudinal axis of the tubular orientation of the base substrate. Fibers applied about the ablumenal surface of a tube with any orientation from slightly helically oriented to longitudinally oriented, that is, oriented at an angle of from 90 to zero degrees with respect to the longitudinal axis of the tube, are herein termed circumferentially oriented. The fibers may be applied as a single layer of a single fiber or multiple fibers, or alternatively may be applied as multiple layers of a single fiber or multiple fibers.

The fibers are most easily applied by placing the base substrate over a snug-fitting mandrel. A fiber or group of fibers is secured to the base substrate near one end by, for example, simply tying the fiber or groups of fibers off to themselves or by securing with a preferably porous film. A rotational force is then applied to the mandrel and the fiber or fibers are paid onto the rotating surface under only slight tension until the desired surface coverage has been achieved.

As described above, the fibers may be circumferentially wound about the ablumenal surface of the base substrate either singly or in groups whereby the fibers are substantially parallel to each other. The fibers may also be helically applied in alternating layers wherein the circumferentially oriented alternating layers are wound in opposing directions as long as fibers applied in this fashion are applied with little tension and are deflectably secured. Fibers helically applied about the ablumenal surface of a base substrate in alternating layers applied in opposing directions are therefore considered to be substantially parallel to each other as well as substantially parallel to the ablumenal surface of the base substrate. The contacting points of adjacent or overlapping fibers are non-adhered or otherwise mechanically connected so as to interfere with their ability to deflect apart from each other.

The fibers may be applied in groups or bundles of several millimeters in width. Such groups of fibers may be applied in the form of, for example, a loose braid wherein fiber groups of at least 1 mm width cross at wide intervals such as about one centimeter apart in a form of interlocking relationship. With the crossover points of the braid being spaced relatively far apart and with the groups of fibers non-adhered or otherwise not directly secured to each other or to the ablumenal surface of the base substrate, the groups of fibers in the portion of their lengths between the crossover points of the braid are capable of deflecting away from a penetrating dialysis needle.

In a further embodiment, the fibers may be in a random, unorganized arrangement such as a mat of fibers wherein the fibers within the mat lie substantially parallel to the ablumenal surface of the base substrate but are not substantially parallel to each other. The individual fibers may cross each other at random intervals but are not in an organized, interlocking arrangement as would exist with a tightly woven or knitted fabric. Such a mat of fibers has a similar appearance to conventional mats of fiberglass fibers. The fiber mat may be wrapped around the ablumenal surface of the base substrate and retained by any suitable means for deflectably securing such as an exterior wrapping of porous film.

The fibers are secured to the ablumenal surface of the base substrate in a manner that allows most of the length of the fibers to be deflected, that is, moved at least slightly with respect to the base substrate. Therefore the fibers may be secured to the ablumenal surface of the base substrate at intervals by mechanical or adhesive or any other suitable means. A preferred method is to wrap a film of porous, biocompatible film about the outer surface of the fibers with enough tension to retain them to the base substrate ablumenal surface in a secure but deflectable manner. This construction also ensures against fibers becoming too loose if the fiber-wrapped portion of the graft is cut as part of a surgical procedure.

The ablumenal surface of the base substrate is not required to be completely covered by the wound fibers; some portion of the base substrate ablumenal surface may be visible between adjacent fibers. Adjacent fibers must be sufficiently close to one another so that they are deflected apart when a dialysis needle is inserted between the adjacent fibers and through the base substrate wall. For minimal blood loss from needle puncture and removal, it is preferred that enough fibers be used to cover the ablumenal surface of the base substrate so that the surface is not visible through the fibers.

In an alternative embodiment, the outer covering of deflectably secured material may be in the form of a porous film wherein the film is preferably applied about the ablumenal surface of the base substrate in the form of a helically wrapped film. The porous film outer covering is deflectably secured in that a substantial portion of the film outer covering is non-adhered or otherwise not directly secured to the ablumenal surface of the base substrate. It is preferred that this type of outer covering is applied in the form of multiple layers of deflectably secured porous film, for example, five or more layers. It is believed that the presence of this type of deflectably secured outer covering serves as a baffle to blood attempting to escape from a dialysis needle hole. The deflectably secured porous film is preferably porous PTFE but alternatively may be of other porous materials such as PET fabric.

In still another alternative the film may be applied with a longitudinal orientation, that is parallel to the longitudinal axis of the tubular form of the base substrate. Again, the film covering may be in the form of multiple layers of deflectably secured film.

An effective vascular graft according to the present invention can also be made by using an outer covering of discrete pieces of material over the surface of a base substrate wherein the pieces are deflectably secured by an exterior wrapping of porous film. The discrete pieces of material are preferably shredded porous PTFE sheet material, however alternative materials such as pieces of PET fabric may also be used. The use of such a deflectably secured covering of discrete pieces and exterior film wrapping again appears to offer a baffling effect to blood attempting to escape from the hole caused by a dialysis needle.

The reduced bleeding characteristic of the inventive vascular graft is believed to be substantially the result of the outer covering of fibers, film, discrete pieces, or combinations thereof, being deflectably secured to the ablumenal surface of the base substrate. Fibers adhered to the ablumenal surface of the base substrate or wrapped about the ablumenal surface of the base substrate under excessive tension are not deflectable with respect to the ablumenal surface when the graft is pierced by a dialysis needle and consequently are much less effective at reducing the amount of blood loss at the cannulation site.

Figure 2:
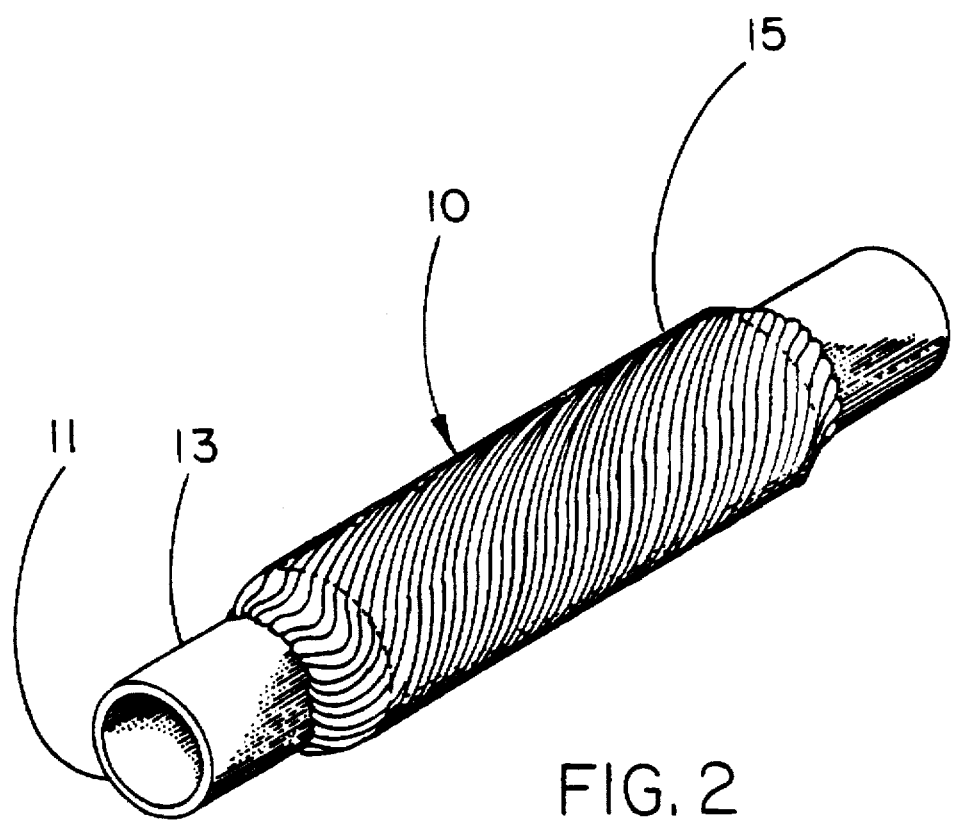
FIG. 2 describes a perspective view of one embodiment of the present invention in the form of a base tube having a substantial portion of its length provided with an outer covering of circumferentially oriented and deflectably secured fibers.

FIG. 1 shows a perspective view of one embodiment of the present invention 10 wherein at least a portion of the length of a base tube 11 has a covering of deflectably secured fibers 15. The fibers 15 are substantially parallel to the ablumenal surface 13 of the base tube 11 and are also substantially parallel to each other. The fibers may be applied in groups so that quantities of the substantially parallel fibers are simultaneously wrapped around the ablumenal surface of the base tube. In the embodiment described by FIG. 1, the fibers are substantially perpendicular to the longitudinal axis of the base tube. Alternatively, the fibers may be provided with a substantial helical orientation such as shown by FIG. 2.

Figure 3:
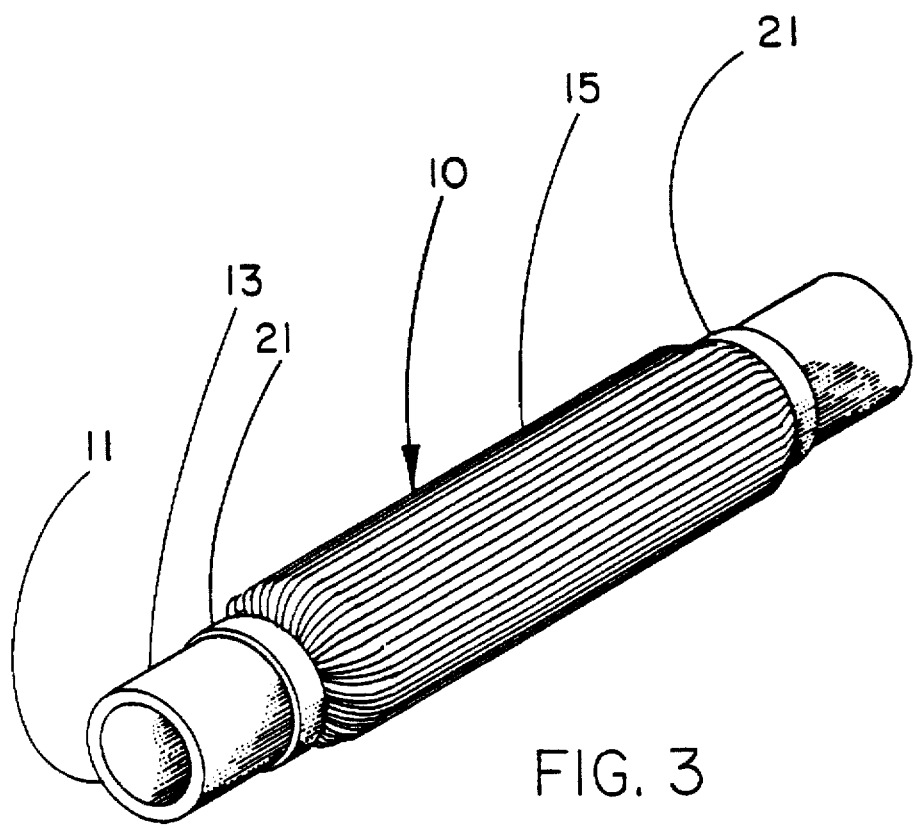
FIG. 3 describes a perspective view of one embodiment of the present invention in the form of a base tube having a substantial portion of its length provided with an outer covering of longitudinally oriented and deflectably secured fibers.

In still another embodiment, the fibers may be applied longitudinally so that they are oriented in a direction substantially parallel to the longitudinal axis of the base tube as shown by FIG. 3. The embodiments described in FIGS. 1, 2 and 3 all have outer coverings of substantially parallel fibers that are collectively termed circumferentially oriented fibers.

The cross section of FIG. 3A describes a variation of the embodiment of FIG. 3 wherein only the ablumenal surface of the graft closest to the patient's skin has been provided with a covering of longitudinally oriented fibers retained by a layer of porous film 17 as will be described.

Figure 4:
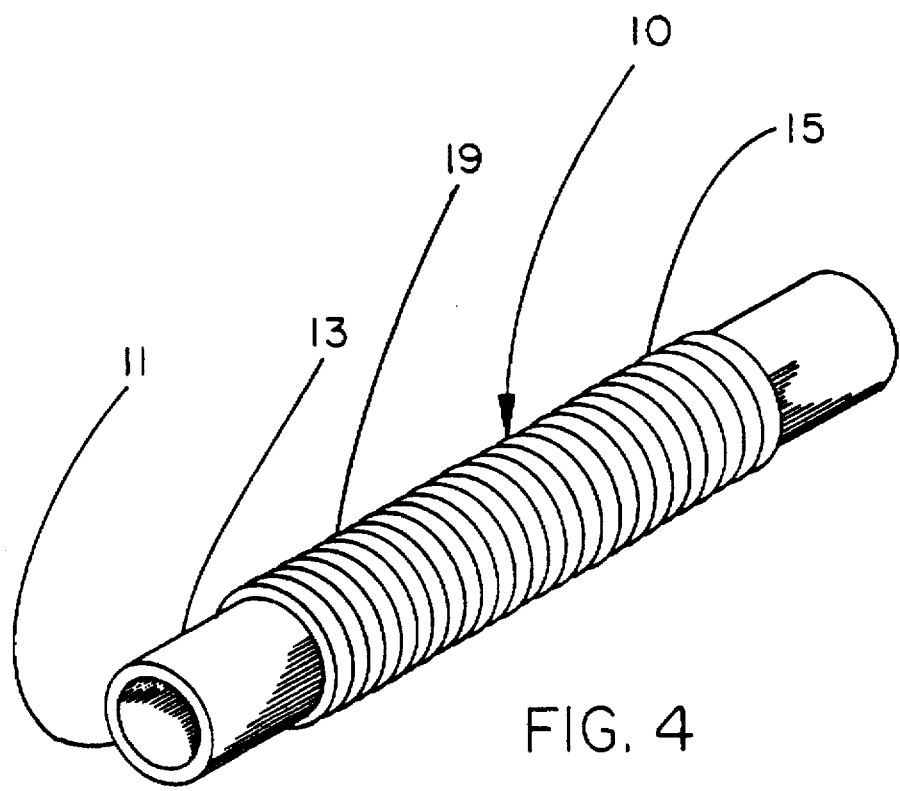
FIG. 4 describes a perspective view of one embodiment of the present invention in the form of a base tube having a portion of its length provided with an outer covering of a circumferentially oriented single layer of deflectably secured fibers applied as a winding about the ablumenal surface of the base tube.

As shown by the perspective view of FIG. 4, the fibers 15 may be applied to the ablumenal surface of the base tube by winding individual fibers 19 around the surface so that the fiber is circumferentially oriented with respect to the base tube and only has enough of a helical orientation to allow adjacent windings to lie close to each other or in direct contact with each other.

Figure 5:
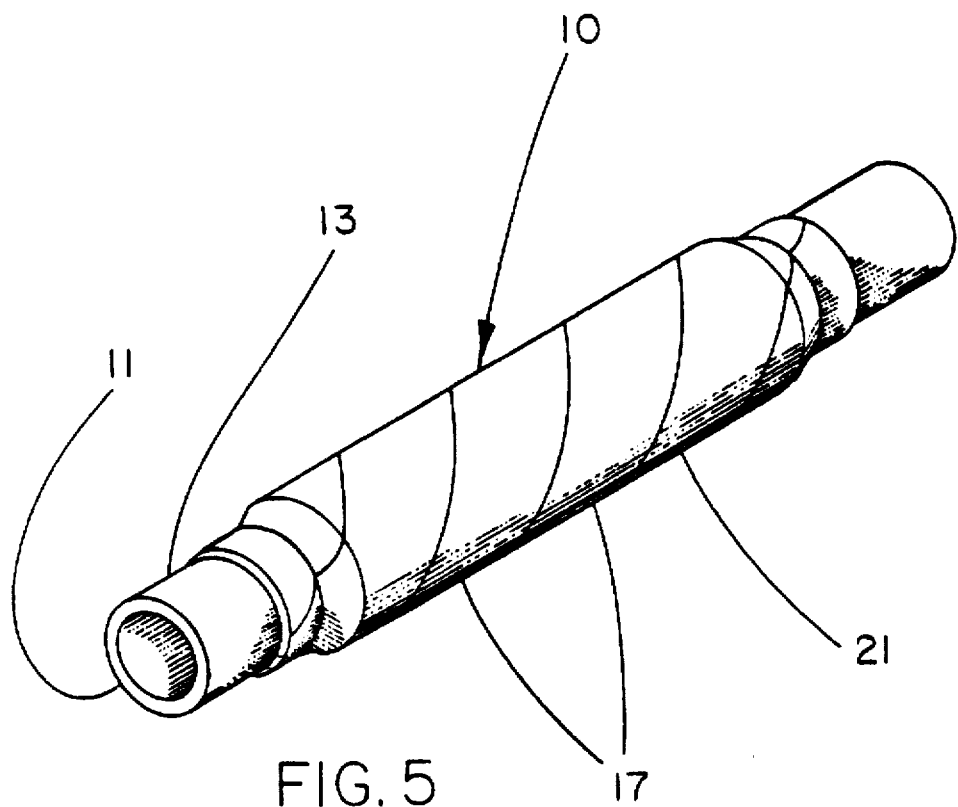
FIG. 5 shows a perspective view of a preferred means for deflectably securing the outer covering by the addition of an exterior wrapping of a thin, porous film about the exterior of the outer covering.

FIG. 5 describes a preferred method of deflectably securing the fibers to the ablumenal surface 13 of the base tube 11 with a wrapping of a porous film 17 that has been cut into a film 21 and helically applied about the outer surface of the fibers. The preferred porous film is a film of porous PTFE as described previously. Examples were made using such a film to deflectably secure the fibers by inserting a stainless steel mandrel through a base tube, loosely wrapping the porous PTFE film about the ablumenal surface of the base tube and placing the resulting assembly into an oven set at 386° C. for a typical period of about two minutes. Heating at this temperature for this amount of time is adequate to begin to cause the PTFE film 21 to retract in length and thereby tighten about the exterior surface of the fibers. This quantity of heat can only be applied to base substrates of entirely PTFE construction. It is also necessary to restrain the base tube longitudinally to prevent shrinkage during heating. Excessive application of heat may result in excessive film shrinkage which will inhibit the ability of the fibers to deflect away from a penetrating needle. The amount of heat applied during the manufacture of the vascular graft of the present invention may be determined by one of ordinary skill in the art as a function of the materials chosen for the desired construction.

FIG. 5 also describes the appearance of the embodiment wherein the deflectably secured material is in the form of a layer of multiple layers of deflectably secured porous film. This embodiment is further described by the cross section of FIG. 5A.

Figure 6:
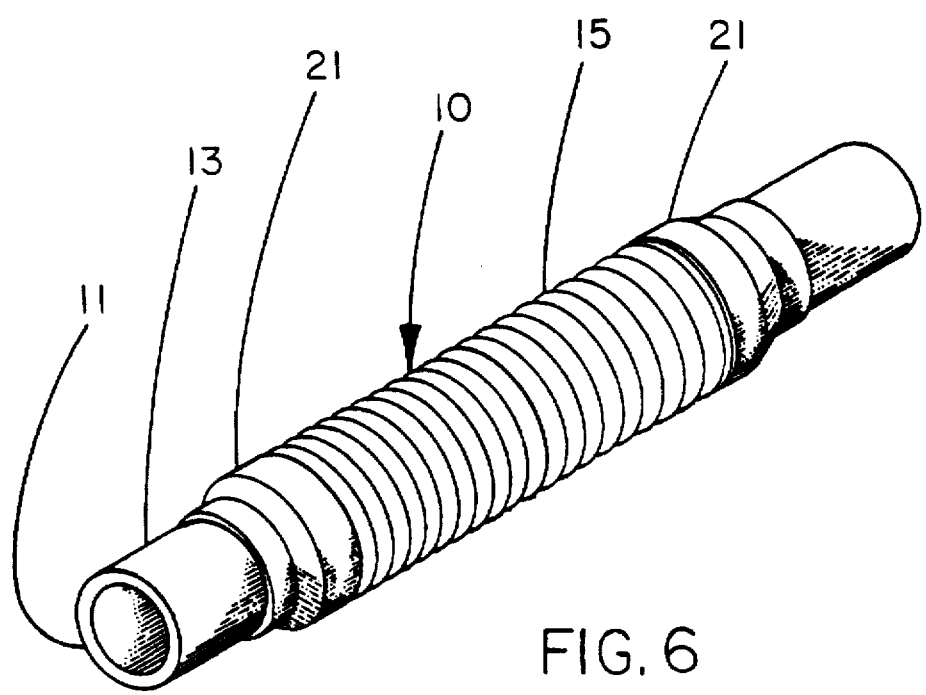
FIG. 6 shows a perspective view of an alternative means for deflectably securing the fibers in the form of an exterior wrapping of film applied only at the fibers ends.

FIG. 6 describes an alternative method of deflectably securing the fibers 15 to the ablumenal surface 13 of the base tube 11 by restraining only the extreme ends of the groups of fibers at the ends of the fiber covered portion of the base tube with film 21.

Figure 7:
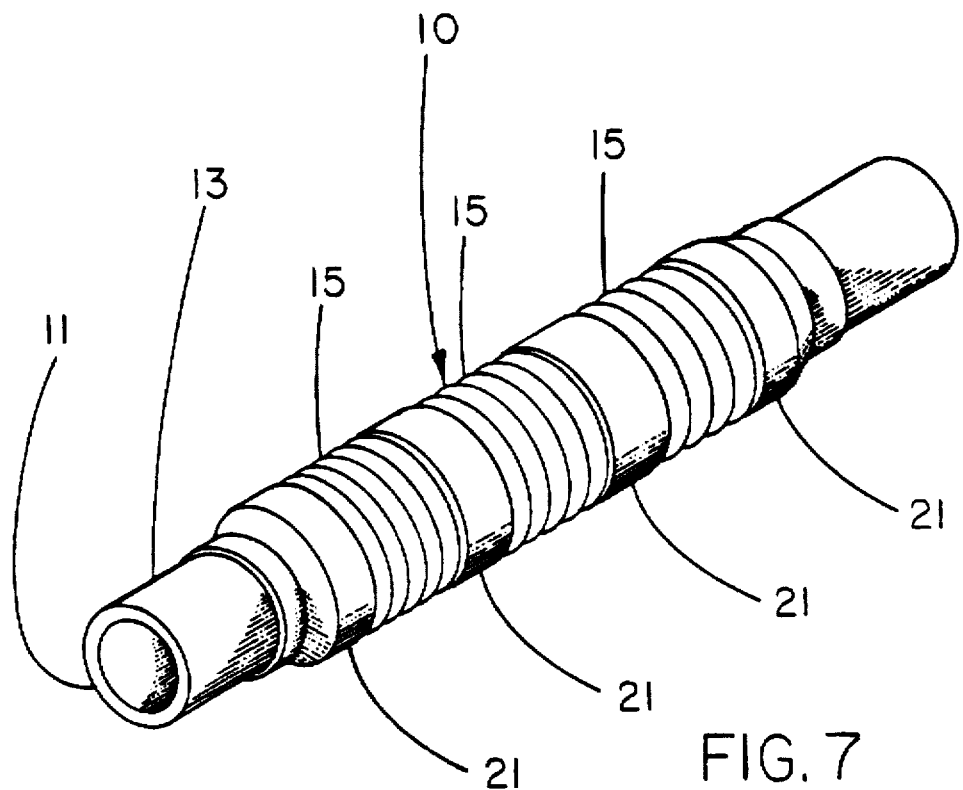
FIG. 7 shows a perspective view of an alternative means for deflectably securing the fibers in the form of an exterior wrapping of film applied at intervals over the fiber covering.

FIG. 7 describes an alternative method of deflectably securing the fibers to the ablumenal surface of the base tube by placing bands of film 21 about the circumference of the base tube at intervals; these bands may be circumferentially oriented or alternatively may be in the form of a helix with wide areas of fibers exposed between adjacent bands or windings of film.

Alternatively, the fibers may be deflectably secured to the ablumenal surface of the base tube by the use of a biocompatible adhesive applied at intervals to points of contact between the fibers and the ablumenal surface of the base tube. If an adhesive is used to secure the fibers to the base tube, it is preferred to apply the adhesive only at the ends of the lengths of the fibers so as to leave the portions of the fibers between the adhesively secured ends free and therefore deflectable. Suitable adhesives include silicone adhesives and thermoplastic fluoropolymer adhesives such as FEP.

Figure 8:
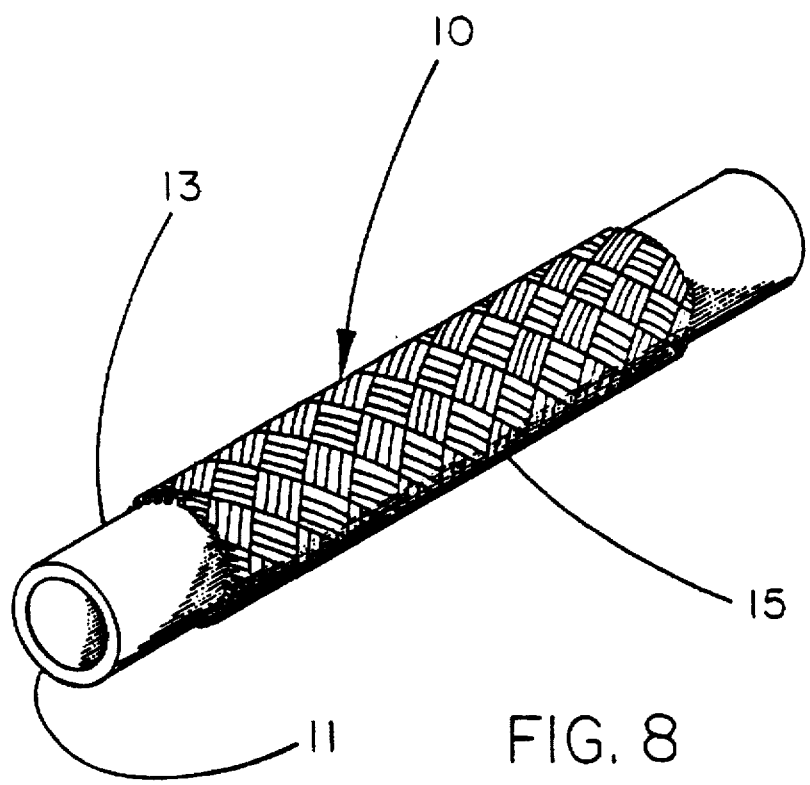
FIG. 8 shows a perspective view of one embodiment of the present invention in the form of a base tube having a substantial portion of its length provided with an outer covering of deflectably secured fibers arranged in a braided construction.
Figure 9:
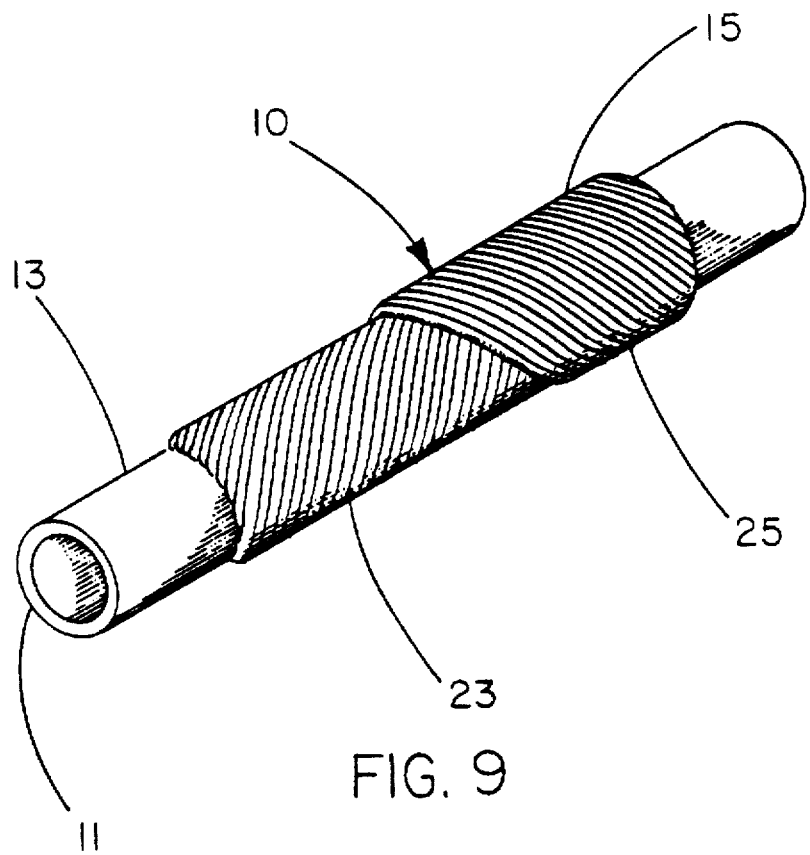
FIG. 9 shows a perspective view of one embodiment of the present invention in the form of a base tube having a substantial portion of its length provided with an outer covering of helically oriented and deflectably secured fibers wherein the fibers have been applied in two helically oriented layers at opposing angles.
Figure 10:
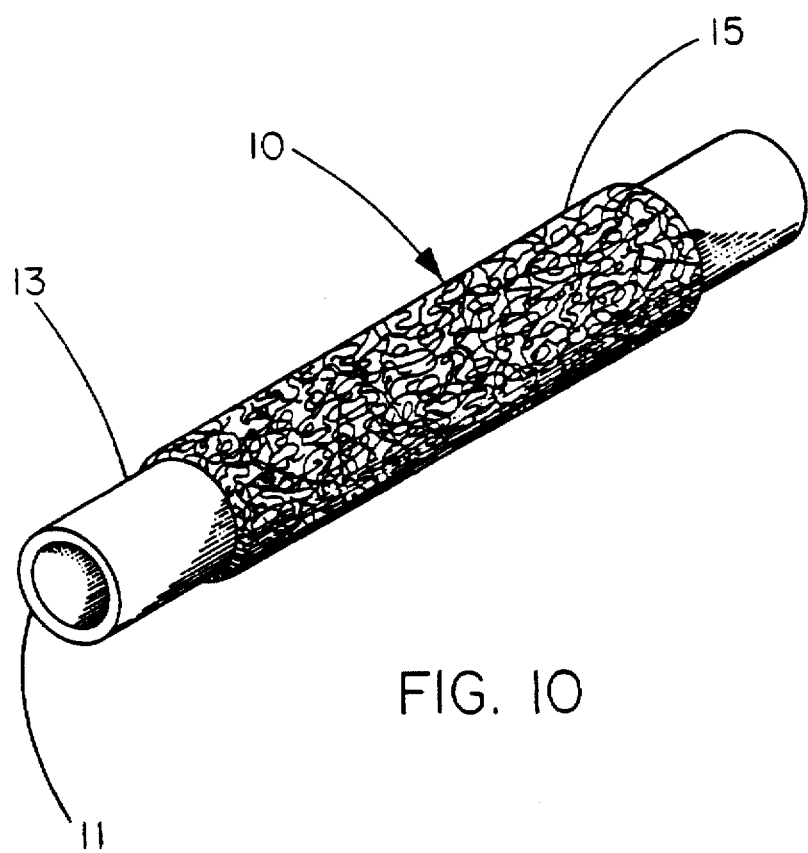
FIG. 10 shows a perspective view of one embodiment of the present invention in the form of a base tube having a substantial portion of its length provided with an outer covering of deflectably secured fibers in the form of an unorganized mat.

FIGS. 8, 9 and 10 describe the use of alternative arrangements of the outer covering of fibers. FIG. 8 describes fibers in an organized braided construction wherein the braided fibers may be deflectably secured to the ablumenal surface of the base tube by any of the previously described methods. Other organized constructions of fibers are possible to include knits and weaves as long as the fibers within the organized construction are deflectably secured to the ablumenal surface of the base tube.

FIG. 9 describes an alternative arrangement of deflectably secured helically oriented fibers 15 wherein a second layer 25 of helically oriented fibers 15 is applied over the first layer 23 of helically oriented fibers at an opposing angle to that of the first layer 23.

FIG. 10 describes the use of an alternative construction of deflectably secured fibers 15 wherein the fibers are arranged in the form of an unorganized mat and deflectably secured to the ablumenal surface of the base tube by any of the previously described methods.

FIG. 11 describes an alternative embodiment of the present invention having a substantial portion of its length provided with an outer covering of discrete pieces 27 of material deflectably secured by an exterior wrapping of porous film 17.

Tubular Vascular Graft Examples

Various inventive graft examples were manufactured by providing different types of base tubes with different types of fiber or film coverings. Some of the fiber covered examples were further provided with an exterior wrapping of porous film. These samples were then tested as described below against a comparative example in the form of a commercially available 6 mm GORE-TEX Vascular Graft (part no. V06040).

The various examples and test results are described by Table I.

All inventive examples except Example 14 were manufactured using approximately 20 cm lengths of 6 mm GORE-TEX Vascular Grafts (part no. V06040) as the base tube. These vascular grafts have a thin wrapping of helically applied porous PTFE film as a reinforcement to prevent aneurysmal dilatation of the graft resulting from the application of blood pressure to the graft over time. All of this film is directly secured as opposed to the deflectably secured films used with the vascular graft of the present invention. The presence of the reinforcing film on the ablumenal surface of the base tube is not believed to be necessary to the reduced bleeding characteristic resulting from the application of an outer covering of deflectably secured materials to a base tube of this type. Example 14 was manufactured using an 8 mm Hemashield® vascular graft (Meadox Medical, Inc., Oakland, N.J., part no. 095408) as the base tube. This base tube is of knitted PET fabric construction and is provided by the manufacturer with a coating intended to reduce leakage of blood through the wall of the fabric.

The fiber outer coverings were typically wrapped around the ablumenal surface of the base tube using only a slight amount of tension. Typically only the center 16 cm portion of the length of each example was provided with a fiber covering. For examples not having an exterior wrapping of film, the ends of the fibers were deflectably secured to the ablumenal surface of the base tube by tying the ends of the fibers about the ablumenal surface of the base tube at each end of the fiber covered portion.

Examples 11 and 13 had fiber coverings and Example 10 had a metal wire covering wherein a small amount of tension was applied to the fibers during the process of wrapping them about the ablumenal surface of the base tube with the result that some compression of the base tube occurred. This amount of tension did not interfere with the deflectably secured character of the fibers as indicated by the leakage results in comparison with the comparative example. The wire covering used for Example 10 was a PTFE insulated 7-strand wire available from W. L. Gore & Associates, Inc., Phoenix, Ariz., part no. IPP-1127.

Where an exterior wrapping of porous PTFE film was provided (Examples 1A, 2A, 3A, 4A, 5A, 6A, 7, 8, 9, 10, 11, 12, 13, 14 and 16), a film of 17 mm width, about 0.01 mm thickness, and about 0.3 g/cc density was used. In comparison to solid, non-porous PTFE having a density of about 2.2 g/cc, the film was about 85% porous by bulk volume. The film was a porous expanded PTFE film made as taught by U.S. Pat. No. 4,187,390. The end of the film was tied about the circumference of the example where it was desired to end the film.

Example 15 was made using an outer covering of multiple layers of the same porous expanded PTFE film used as an exterior wrapping. At least 70 layers of this film, as counted through a transverse cross section of the tube, were loosely applied about the ablumenal surface of the base tube.

All of the examples constructed from a PTFE base tube having a covering of PTFE fibers and provided with an exterior wrapping of porous PTFE film were heated to cause shrinkage of the outer porous PTFE film covering as described previously.

Examples 2, 3, 5 and 6 were all two-part examples made by providing the central approximately 16 cm length portion of the base tube with a fiber covering as described and subsequently providing one half of the fiber covered portion with an exterior wrapping of porous PTFE film. The respective 8 cm long halves of these examples were tested separately by clamping off the half of the length of the example to be tested with a forceps applied at the midpoint of the example and thereby isolating the opposite half.

Example 16 used an outer covering of shredded discrete pieces of porous PTFE of varying sizes and shape. The pieces were the result of shredding GORE-TEX Vascular Grafts. The pieces ranged from about 0.5 mm square to approximately rectangular shapes of about 2 mm by 4 mm and were most typically of about 1 mm by 1 mm size and about 0.5 mm thickness. The shredded material was applied and deflectably secured to the ablumenal surface of a base tube by wrapping the base tube with porous PTFE film while simultaneously feeding the shredded pieces of porous PTFE onto the inner surface of the film during wrapping.

The Du Pont Teflon Packing Yarn used in Example 1A and 1B was from E.I. Du Pont de Nemours, Wilmington, Del. The acrylic yarn used for Examples 2A and 2B was from Lee-Wards, Elgin, Ill., as part no. 26-05806. The Spectra 700 Fiber used for Examples 3A and 3B was obtained from Allied Signal, Inc., New York, N.Y. GORE-TEX® fibers used for Examples 4A, 4B, 5A, 5B, 6A, 6B, 7, 8, 9, 12 and 14, and GORE-TEX® Sewing Thread used for Example 11 are available from W. L. Gore & Associates, Inc., Elkton, Md.; GORE-TEX® Suture used for Example 13 is available from W. L. Gore & Associates, Inc., Flagstaff, Ariz.

Testing consisted of pressurizing each example individually with water at 150 mm Hg at room temperature, cannulating the example with a 15 gauge dialysis needle, removing the needle and applying digital pressure to the needle hole for a short period, typically about 15 seconds, after which the volume of water escaping from the needle hole during a 15 second period was measured. A vertical water column was used to supply the pressure for this leak-testing of each example. Each example was hand-held in a horizontal position and tested at the same elevation with respect to the water column. The example graft was connected to the base of the water column by a short length of tubing using a clamp to prevent water leakage at the graft/tubing connection. The opposite end of the example graft was clamped closed using a forceps. None of the tested examples leaked any water prior to cannulation. The fiber covered portion of each example graft was cannulated with a new 15 gauge, 1.80×25 mm dialysis needle (Terumo Medical Corp., Elkton, Md., code no. AV*E15); the needle was then removed and digital pressure was applied to the location of the needle hole. After removal of digital pressure from the cannulation site, the water leaking from the site for a 15 second period was captured in a tray. The water in the tray was then transferred to a graduated cylinder to measure volume.

Cannulation was accomplished by inserting the point of the needle into an upper surface of the graft with the bevel of the needle facing upwards, that is, away from the surface of the graft. The point of the needle was inserted through the graft so as to intersect the longitudinal axis of the graft. The needle was always aligned with the graft so that the longitudinal axis of the needle and the longitudinal axis of the vascular graft lay in a common plane during cannulation. Each needle was oriented at an angle of about 45 degrees with respect to the longitudinal axis of the graft. Care was taken not to damage the opposite or lower surface of any tested example during cannulation of the upper surface.

The results of the leakage tests for various comparative and inventive examples are described in Table 1. Example 13 was cannulated and measured three times by clamping off with forceps a previous cannulation site and repeating the puncturing and measuring procedure. A single cannulation was performed on all other examples.

The Table 1 column under the heading of "Figure Reference" describes the general appearance of each example. Where two figures are referred to, the first describes the appearance of the graft after being provided with an outer covering of fibers and the second describes the appearance of the same sample after it was subsequently provided with an exterior wrapping of porous PTFE film. The column under the heading "Orientation of Covering" relates to the orientation of the outer covering prior to the application of any exterior wrapping of porous PTFE film. Only for the purposes of this column of Table 1, the term circumferentially is used to describe fibers oriented at an angle of about 90 degrees to the longitudinal axis of the tube, helically is used to describe fibers oriented at angles of about 45 degrees with respect to the longitudinal axis of the tube and longitudinal is used to describe fibers oriented approximately parallel to the longitudinal axis of the tube. N/A within the table is used to mean "not applicable."

Acute Animal Example

A fiber covered vascular graft of the present invention and a comparative conventional porous PTFE vascular graft were implanted into a 27 kg greyhound dog as arteriovenous shunts between the animal's femoral arteries and veins to compare blood loss resulting from cannulation of the grafts with a dialysis needle. The inventive example was of the same type described previously as Example 4a and was anastomosed between the animal's right femoral artery and vein. The fiber covered portion of the inventive example extended over about the center 15 cm portion of the length of the inventive example, leaving a 2-3 cm length of base tube not having a fiber covering extending beyond each end of the fiber covered portion. A 20 cm length of GORE-TEX Vascular Graft of the same type used for the comparative example in Table 1, part no. V06040, was anastomosed as a comparative example between the animal's left femoral artery and vein. Cannulation tests of the comparative and inventive examples were performed as described below on the exposed vascular grafts. These implants were considered to represent a worst case bleeding situation because the exposed vascular grafts were directly cannulated as opposed to being cannulated subcutaneously after a healing period.

The implantation procedure began by making incisions adequate to expose the femoral arteries and veins of both legs of the animal. 100 units of heparin per kg of body weight were administered intravenously and allowed to circulate for approximately 10 minutes. The femoral arteries and veins were clamped off during the implantation procedure which involved end-to-side anastomoses fashioned using conventional vascular surgery techniques and CV-6 GORE-TEX Sutures. Clamp times were approximately 30 minutes for the placement of each arteriovenous shunt. After releasing the clamps the shunts were exposed to the flow of heparinized blood for more than 10 minutes. The anticoagulant effect of heparin was then reversed by the intravenous administration of protamine sulfate in the quantity of 1 mg of protamine sulfate per 100 units of heparin. An additional 15 minutes was allowed to elapse in order to allow the protamine sulfate to take effect and stabilize. The surgical wounds created to provide access to the femoral veins and arteries were left open during the subsequent cannulation of the examples with dialysis needles. 6 mm ultrasonic flow probes were placed around the femoral arteries at sites just proximal and just distal to the anastomoses of the shunts. The blood flow through each shunt was then monitored by subtracting the flow in the distal femoral artery segment from the flow in the femoral arterial segment proximal to the shunt anastomosis. Systemic arterial pressure was constantly monitored during cannulation of the shunts. The systemic arterial pressure and the measured and calculated blood flows showed little change during the course of the experiment with systemic arterial pressure remaining in the 85-95 mm Hg range and the flow through the individual shunts remaining in the 900-1000 ml/min range.

The cannulation tests were performed by inserting Terumo dialysis needles (Elkton, Md., code AV*E15) through the uppermost wall of the shunt using conventional cannulation techniques, removing the needle, and observing the relative volume of the subsequent hemorrhage from the needle puncture site. For several cannulations, digital pressure was applied to the puncture site for 60 seconds after removal of the needle.

Multiple puncture sites were individually made in the inventive example; a single puncture site was made in the comparative 6 mm GORE-TEX Vascular Graft. Finally, simultaneous punctures were made in the fiber covered portion of the inventive example and in the proximal end of the inventive example near the anastomosis not having the fiber covering, that is, a portion of the inventive graft that represented the comparative 6 mm GORE-TEX Vascular Graft.

All needle punctures in the fiber-covered portion of the inventive graft stopped bleeding within one minute or less regardless of the application of any digital pressure to the puncture site. The single puncture in the comparative 6 mm GORE-TEX Vascular Graft produced a vigorous stream of blood ejected from the puncture site, regardless of the use or lack of digital pressure. There was no evidence of any reduction in the quantity of bleeding from the puncture site after observation for one full minute. Vascular clamps were then placed on this shunt proximal and distal to the puncture site.

The simultaneous punctures of the fiber covered and uncovered portions of the inventive example resulted in hemostasis within one minute for the fiber covered portion, and a vigorous stream of blood ejected from the puncture site not having the fiber covering. This stream of blood showed no sign of reduction and consequently required active intervention to stem the flow of blood.

Flat Sheet Patch Examples

While these inventive examples were constructed only in the form of flat sheet vascular grafts, it is apparent that inventive examples of this type of construction would also be effective as tubular vascular grafts. It is also apparent that flat sheet vascular grafts may be made by slitting tubular vascular grafts longitudinally.

GORE-TEX Cardiovascular Patches of 0.4 mm thickness, 2 cm width and 9 cm length (product no. 1802009004, W. L. Gore & Associates, Inc. Flagstaff, Ariz.) were used for these examples. Two of these GORE-TEX Cardiovascular Patches were modified by deflectably securing multiple layers of a porous film in the form of a layer of porous expanded PTFE having a discontinuous FEP adhesive on one surface. By discontinuous is meant that the FEP is in the form of separate, discrete areas of FEP separated by substantial areas of the porous PTFE film not covered by the FEP. Additionally, the discontinuous character of the FEP results in the film retaining its porosity between the FEP-covered areas. The film of porous PTFE and discontinuous FEP was made by a process which comprises the steps of:

a) contacting a porous PTFE substrate, usually in the form of a membrane or film, with another layer which is preferably a film, of FEP or alternatively another thermoplastic polymer;

b) heating the composition obtained in step a) to a temperature above the melting point of the thermoplastic polymer;

c) stretching the heated composition of step b) while maintaining the temperature above the melting point of the thermoplastic polymer; and d) cooling the product of step c).

In addition to FEP, other thermoplastic polymers including thermoplastic fluoropolymers may also be used to make this porous film.

The porous films used to make examples of the present invention had a thickness of about 0.01 mm, a density of about 0.3 g/cc and a width of about 17 mm. These films used FEP as the discontinuous thermoplastic fluoropolymer adhesive. Examination of the FEP side of the film by scanning electron microscopy revealed FEP on only small portions of the nodes and fibrils at the surface of the film. It was estimated that less than 10% of the available node and fibril surface area exposed at the surface of the film was covered by FEP. The presence of the FEP adhesive thus had little or no adverse effect on the porosity of the porous PTFE layer of the film.

Example 17 was made by wrapping a 2 cm×9 cm GORE-TEX Cardiovascular Patch around the circumference of a 28 mm diameter stainless steel mandrel with the 2 cm dimension of the patch oriented parallel to the longitudinal axis of the mandrel. A 12.5 mm wide length of the film was wrapped around the patch and mandrel with the discontinuous FEP-covered side of the film in contact with the patch. The film was helically and loosely wrapped around the surface of the sheet of patch material at alternating and opposing angles of about 80 degrees with respect to the longitudinal axis of the mandrel. A single pass of wrapping this film about the patch in one direction prior to reversing the wrapping direction and wrapping angle to begin a second pass resulted in overlapping layers of film to the extent that a total thickness of about five overlapping layers of film existed as measured by counting layers through a transverse cross section. A total of eight passes were applied resulting in a total of about 40 layers of film applied over the patch and mandrel. The resulting mandrel, patch and film assembly was then placed into an oven set at 325° C. for 30 minutes, after which it was removed from the oven and allowed to cool to room temperature. The film spanning the edges of the patch was then cut, allowing the patch to be removed from the surface of the mandrel and returned to the form of a flat sheet now having a covering of forty layers of film on one side.

A second patch, Example 18, was made in the same manner except that it was placed into the oven for heating after the application of only 4 passes and about 20 layers of film. After removal from the oven and cooling, the patch was cut free from the mandrel, turned 90° with respect to the mandrel, and refitted to the surface of the mandrel, after which an additional 4 passes and about 20 layers of film were helically and loosely applied. The mandrel, patch and film assembly was again heated, cooled and the film covered patch was removed from the mandrel as described previously. The resulting patch thus had about 40 layers of film deflectably secured to one surface with the outer 20 layers having a fibrillar microstructure oriented at about 90° to the microstructure of the inner 20 layers. Both of the film covered patches had a slightly wrinkled appearance on the film-covered side. Flexing or bending the patch produced slight movement of the wrinkles, indicating that adjacent layers of film were non-adhered except at occasional points of contact where the discontinuous FEP-covered PTFE microstructure had thermally bonded to the adjacent layer of film by melting of the FEP during the heating step.

Figure 12:
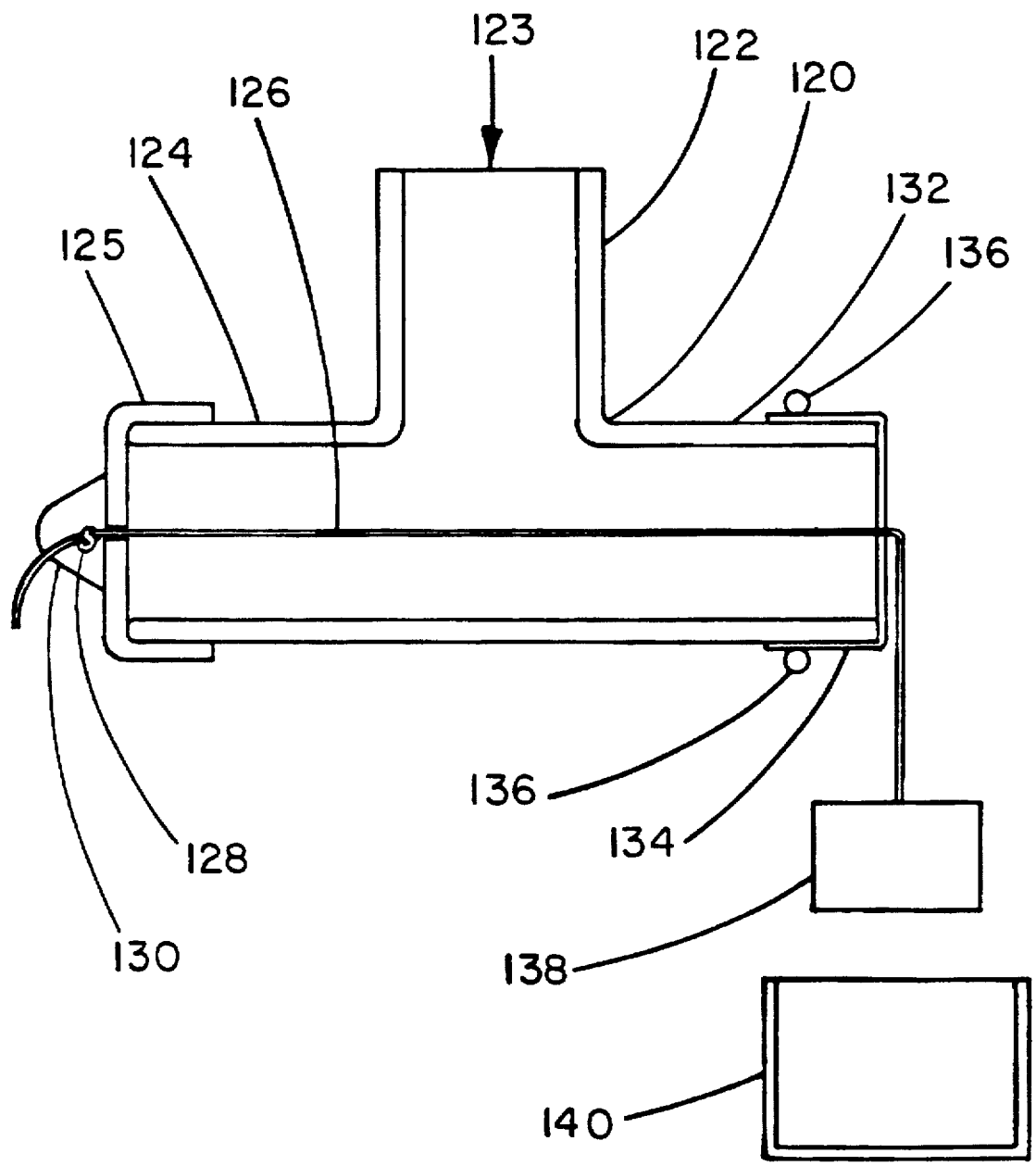
FIG. 12 describes a cross sectional view of a test fixture for testing flat sheet vascular grafts for water leakage through a suture needle hole.

The two patches described above were tested for suture hole leakage at room temperature in comparison to an unmodified GORE-TEX Cardiovascular Patch product no. 1802009004. As shown by FIG. 12, a tee-shaped pipe test fixture 120 of about 1.3 cm inside diameter and 1.6 cm outside diameter was created with the center leg 122 of the tee connected to the 150 mm Hg pressure water column 123 used previously for testing tubular vascular grafts. One end 124 of the tee 120 was provided with a cap 125 having a small, centrally located hole through which one end of a length of CV-6 GORE-TEX Suture 126 had been placed. A knot 128 was tied in the suture 126 exterior to the cap 125 to retain it in place and a small amount of elastomeric sealant 130 was placed over the knot and adjacent cap 125 to prevent water leakage. The remaining end 132 of the pipe tee 120 was covered by the patch 134 to be tested with the patch 134 secured to the end 132 of the pipe tee 120 by a wire clamp 136. Prior to fitting the patch 134 to the pipe tee 120, a TT-9 taper point suture needle attached to the previously described suture 126 was used to pierce the center, film-covered portion of the patch 134 and pull the length of suture 126 through the approximate center of the patch 134. This TT-9 needle had a maximum diameter of about 0.25 mm. The patch 134 was then fitted to the end 132 of the tee-shaped pipe test fixture 120 as described with the film-covered side of the patch 134 oriented to face outwardly away from the tee 120. A 100 gram weight 138 was hung from the exposed end of the suture 136 so that the weight 138 applied a load parallel to the pressurized surface of the patch 134 and perpendicular to the horizontally oriented length of suture 126 within the test fixture 120. A beaker 140 was placed under the weighted end of the suture 126 for 1.0 minutes to capture water leaking through the suture hole. The volume of captured water was then measured in a graduated cylinder. The quantitative water leakage results measured in ml/minute were as follows: Control: 13 ml; Example 17: 4 ml; Example 18: 0.5 ml.

It is apparent that the inventive vascular grafts, particularly in the form of flat sheet vascular grafts, may be provided with a deflectably secured covering on both surfaces. Additionally, both tubular and flat sheet vascular grafts may be constructed in the form of a laminate of three fundamental layers wherein the middle of the three layers comprises deflectably secured material. The other two layers may be in the form of conventional vascular graft base substrate materials.

It is believed that both flat sheet and tubular vascular grafts made with the film described above will reduce bleeding from both suture and dialysis needle holes.

4. The vascular graft of claim 1 wherein said at least one fiber comprises a biocompatible material selected from the group consisting of polytetrafluoroethylene, polyethylene terephthalate and biologic material.

TABLE 1

| Example | Type of Outer Covering | Thickness of Covering | Approx. Finished OD | Outer Layer of Film | Heating | Water Leak ml/15 sec | FIG. Refer. | Orientation of Covering |
|---|---|---|---|---|---|---|---|---|
| Comparative | None | N/A | 7.4 mm | No | No | 63 ml | N/A | N/A |
| 1A | Dupont Teflon Packing Yarn Part No. 1T004 | 0.9 mm | 9.2 mm | Yes | 386° C., 2 min | 10 ml | 1, 5 | Circumferential |
| 1B | Dupont Teflon Packing Yarn Part No. 1T004 | 1.0 mm | 9.4 mm | No | No | 10 ml | 1 | Circumferential |
| 2A | 100% Acrylic 4-ply Yarn 2.5 mm Twisted Fiber | 2.0 mm | 11.4 mm | Yes | No | 6 ml | 4, 5 | Circumferential |
| 2B | 100% Acrylic 4-ply Yarn 2.5 mm Twisted Fiber | 2.2 mm | 11.8 mm | No | No | 10 ml | 4 | Circumferential |
| 3A | Spectra 700 Fibers | 0.8 mm | 9.0 mm | Yes | No | 10 ml | 1, 5 | Circumferential |
| 3B | Spectra 700 Fibers | 0.8 mm | 9.0 mm | No | No | 12 ml | 1 | Circumferential |
| 4A | GORE-TEX Fiber Part No. V112170 | 1.0 mm | 9.4 mm | Yes | 386° C., 2 min | 7 ml | 1, 5 | Circumferential |
| 4B | GORE-TEX Fiber Part No. V112170 | 1.0 mm | 9.4 mm | No | 386° C., 2 min | 5 ml | 1 | Circumferential |
| 5A | GORE-TEX Fiber Part No. V112169 | 1.0 mm | 9.4 mm | Yes | 386° C., 2 min | 12 ml | 1, 5 | Circumferential |
| 5B | GORE-TEX Fiber Part No. V112169 | 1.0 mm | 9.4 mm | No | 386° C., 2 min | 11 ml | 1 | Circumferential |
| 6A | GORE-TEX Fiber Part No. V112169 | 1.15 mm | 9.7 mm | Yes | 386° C., 2 min | 5 ml | 2, 5 | Helical ~45° Altern. Layers |
| 6B | GORE-TEX Fiber Part No. V112169 | 1.25 mm | 9.9 mm | No | 386° C., 2 min | 14 ml | 2 | Helical ~45° Altern. Layers |
| 7 | GORE-TEX Fiber Part No. V112169 | 1.2 mm | 9.8 mm | Yes | 386° C., 2 min | 8 ml | 3, 5 | Longitudinal |
| 8 | GORE-TEX Fiber Part No. V112169 | 0.25 mm | 7.9 mm | Yes | 386° C., 2 min | 5 ml | 1, 5 | Circumferential |
| 9 | GORE-TEX Fiber Part No. V112169 | 0.18 mm | 7.8 mm | Yes | 386° C., 2 min | 1 ml | 1, 5 | Circumferential |
| 10 | PTFE Insulated 7-strand Metal Wire 0.25 mm dia. | 0.25 mm | 7.7 mm | Yes | 386° C., 2 min | 14 ml | 4, 5 | Circumferential |
| 11 | GORE-TEX Sewing Thread Part No. M1000 | 0.1 mm | 7.2 mm | Yes | 386° C., 2 min | 15 ml | 4, 5 | Circumferential |
| 12 | GORE-TEX Fiber Part No. V096T0 | 0.8 mm | 9.0 mm | Yes | 386° C., 2 min | 13 ml | 10, 5 | Mat Form |
| 13 | GORE-TEX Suture Part No. CV-7 | 0.1 mm | 7.4 mm | Yes | 386° C., 2 min | 11, 14, 21 ml | 4, 5 | Circumferential |
| 14 | GORE-TEX Fiber Part No. V112169 | 1.0 mm | 11.2 mm | Yes | No | 10 ml | 1, 5 | Circumferential |
| 15 | Porous PTFE Film | 0.7 mm | 8.8 mm | Yes | No | 8 ml | 5 | Circumferential |
| 16 | Shredded Pieces of Porous PTFE | 1.8 mm | 11.0 mm | Yes | 386° C., 2 min | 17 ml | 11, 5 | Random Distrib. |

We claim:

1. A vascular graft comprising:
   a) a biocompatible base substrate having a lumenal and ablumenal surface; and
   b) a biocompatible material covering a substantial portion of the ablumenal surface of said substrate, said biocompatible material being secured to said ablumenal surface at at least one point and being deflectable with respect to said ablumenal surface,
   wherein said biocompatible material comprises at least one fiber having a surface, wherein said at least one fiber is arranged such that various portions of the surface may be adjacent to each other, and wherein a substantial portion of said various adjacent surface portions are free to move with respect to each other.

2. The vascular graft of claim 1 in which said material covering said ablumenal surface comprises at least two fibers.

3. The vascular graft of claim 1 wherein said at least one fiber comprises a non-elastomeric fiber.

5. The vascular graft of claim 4 wherein said at least one fiber comprises porous polytetrafluoroethylene.

6. The vascular graft of claim 1 in which said base substrate is in the form of a tube.

7. The vascular graft of claim 6 wherein the at least one fiber is oriented parallel to the base substrate.

8. The vascular graft of claim 6 wherein said tube has a longitudinal axis and wherein said at least one fiber is oriented substantially perpendicular to the longitudinal axis.

9. The vascular graft of claim 8 wherein said at least one fiber is comprised of porous polytetrafluoroethylene.

10. The vascular graft of claim 6 wherein said tube has a longitudinal axis and wherein said at least one fiber is oriented substantially parallel to the longitudinal axis.

11. The vascular graft of claim 10 wherein said at least one fiber is comprised of porous polytetrafluoroethylene.

12. The vascular graft of claim 1 in which said material is secured to said ablumenal surface at at least one point by adhesive means.

13. The vascular graft of claim 12 in which said adhesive means comprises an adhesive selected from the group consisting of silicone, fluorinated ethylene propylene and perfluoroalkoxy.

14. The vascular graft of claim 1 wherein the at least one fiber is oriented parallel to the base substrate.

15. The vascular graft of claim 14 wherein the at least one fiber comprises a plurality of fibers oriented substantially parallel to each other.

16. The vascular graft of claim 1 wherein the at least one fiber is arranged in a construction selected from the group consisting of weaves, knits, braids and mats.

17. The vascular graft of claim 1 in which said material is secured to said ablumenal surface at at least one point by adhesive means.

18. The vascular graft of claim 17 in which said adhesive means comprises an adhesive selected from the group consisting of silicone, fluorinated ethylene propylene and perfluoroalkoxy.

19. The vascular graft of claim 1 wherein said biocompatible base substrate is selected from the group of biocompatible base substrates consisting of polytetrafluoroethylene, polyethylene terephthalate and biologic materials.

20. The vascular graft of claim 19 wherein said biocompatible base substrate comprises porous polytetrafluoroethylene.

21. The vascular graft of claim 20 wherein said biocompatible base substrate comprises a porous polytetrafluoroethylene tube.

22. The vascular graft of claim 21 wherein said porous polytetrafluoroethylene tube at ambient temperature is capable of being stretched and rapidly recovering more than about 10 percent of its stretched length.

23. The vascular graft of claim 19 wherein said biocompatible material is selected from the group of biocompatible materials consisting of polytetrafluoroethylene, polyethylene terephthalate and biologic materials.

24. The vascular graft of claim 23 wherein said biocompatible material comprises porous polytetrafluoroethylene.

25. The vascular graft of claim 1 wherein said biocompatible material is selected from the group of biocompatible materials consisting of polytetrafluoroethylene, polyethylene terephthalate and biologic materials.

26. The vascular graft of claim 25 wherein said biocompatible material comprises porous polytetrafluoroethylene.

* * * * *